(12) United States Patent
Zumbrum et al.

(10) Patent No.: US 11,506,310 B2
(45) Date of Patent: Nov. 22, 2022

(54) FLUID TRANSFER ASSEMBLY

(71) Applicant: Sartorius Stedim North America Inc., Bohemia, NY (US)

(72) Inventors: Michael A. Zumbrum, New Oxford, PA (US); Kevin Perdue, Havre de Grace, MD (US); Marc Sanchez, Brooklyn, NY (US); Jan Neuhaus, Dransfeld (DE)

(73) Assignee: Sartorius Stedim North America Inc., Bohemia, NY (US)

( * ) Notice: Subject to any disclaimer, the term of this patent is extended or adjusted under 35 U.S.C. 154(b) by 0 days.

(21) Appl. No.: 16/964,459

(22) PCT Filed: Jan. 24, 2018

(86) PCT No.: PCT/US2018/014947
§ 371 (c)(1),
(2) Date: Jul. 23, 2020

(87) PCT Pub. No.: WO2019/147223
PCT Pub. Date: Aug. 1, 2019

(65) Prior Publication Data
US 2021/0048127 A1 Feb. 18, 2021

(51) Int. Cl.
*F16L 13/16* (2006.01)
*F16L 13/14* (2006.01)
*F16L 33/207* (2006.01)

(52) U.S. Cl.
CPC .......... *F16L 13/161* (2013.01); *F16L 13/142* (2013.01); *F16L 33/2071* (2013.01)

(58) Field of Classification Search
CPC ... F16L 13/161; F16L 13/142; F16L 33/2071; F16L 33/2078; A61M 39/12
(Continued)

(56) References Cited

U.S. PATENT DOCUMENTS 2,139,745 A * 12/1938 Goodall ................. F16L 33/23
285/253
2,766,518 A   10/1956 Costanzo
(Continued)

FOREIGN PATENT DOCUMENTS

DE   29920371 U1 *  1/2000  .......... F16L 33/2078
EP   2677223         12/2013
(Continued)

OTHER PUBLICATIONS

International Search Report and the Written Opinion of the International Searching Authority for PCT/US2018/014947; dated Mar. 26, 2018.
(Continued)

*Primary Examiner* — David Bochna
(74) *Attorney, Agent, or Firm* — Womble Bond Dickinson (US) LLP

(57) ABSTRACT

A fluid transfer assembly is described that includes a fitting comprising a lumen having an opening, and at least one barb, the at least one barb extending circumferentially around the lumen proximate to the opening. The assembly also includes a flexible conduit, a deformable sleeve, and an elastomeric liner disposed between the sleeve and the conduit. The fitting extends at least partially into the conduit such that the conduit extends over the at least one barb. The elastomeric liner applies substantially 360 degree radial pressure to the conduit such that the conduit is sealingly compressed around the at least one barb of the fitting. The assembly is fluid tight up to a burst pressure of the conduit.

15 Claims, 5 Drawing Sheets

(58) Field of Classification Search
USPC .................. 285/256, 296.1, 294.3, 294.4
See application file for complete search history.

(56) References Cited

U.S. PATENT DOCUMENTS

| | | | | |
|---|---|---|---|---|
| 3,516,690 | A * | 6/1970 | Kreig | F16L 13/0236 285/369 |
| 3,794,360 | A | 2/1974 | Bachle et al. | |
| 3,893,718 | A * | 7/1975 | Powell | F16L 13/142 285/53 |
| 4,330,142 | A * | 5/1982 | Paini | B21C 37/20 285/253 |
| 4,498,691 | A * | 2/1985 | Cooke | F16L 33/2076 285/12 |
| 4,603,890 | A * | 8/1986 | Huppee | F16L 33/30 285/14 |
| 4,643,465 | A * | 2/1987 | Green | F16L 21/005 285/236 |
| 4,660,867 | A * | 4/1987 | Kemper | F16L 33/2076 156/294 |
| 5,040,830 | A * | 8/1991 | Atkinson | F16L 33/22 285/256 |
| 5,165,733 | A * | 11/1992 | Sampson | F16L 33/00 285/253 |
| 5,228,721 | A * | 7/1993 | Whittle | F16L 33/2071 285/23 |
| 5,267,758 | A | 12/1993 | Shah et al. | |
| 5,358,012 | A | 10/1994 | Kish | |
| 5,829,795 | A * | 11/1998 | Riesselmann | F16L 33/2078 285/256 |
| 5,853,202 | A * | 12/1998 | Li | F16L 33/30 285/256 |
| 5,868,435 | A * | 2/1999 | Bartholomew | F16L 33/2071 285/23 |
| 5,901,987 | A * | 5/1999 | Godeau | F16L 21/03 285/294.3 |
| 6,012,743 | A * | 1/2000 | Godeau | F16L 33/34 285/294.3 |
| 8,118,331 | B2 * | 2/2012 | Yamashita | F16L 13/147 285/256 |
| 8,393,647 | B2 | 3/2013 | Webster et al. | |
| 9,388,927 | B2 * | 7/2016 | Shmelev | F16L 33/2071 |

| | | | | |
|---|---|---|---|---|
| 2004/0227344 | A1 * | 11/2004 | Lin | F16L 33/2071 285/256 |
| 2005/0082826 | A1 | 4/2005 | Werth | |
| 2005/0161939 | A1 | 7/2005 | Poll | |
| 2008/0136176 | A1 * | 6/2008 | Katayama | F16L 13/142 285/256 |
| 2009/0179422 | A1 * | 7/2009 | Werth | F16L 33/2071 285/243 |
| 2009/0212559 | A1 | 8/2009 | Werth | |
| 2010/0025986 | A1 | 2/2010 | Seton-Anderson | |
| 2012/0042503 | A1 | 2/2012 | Zeiber | |
| 2013/0327432 | A1 | 12/2013 | McMurray et al. | |
| 2015/0035276 | A1 | 2/2015 | Shmelev | |
| 2016/0305577 | A1 | 10/2016 | Huschke | |
| 2017/0314719 | A1 | 11/2017 | Blake et al. | |

FOREIGN PATENT DOCUMENTS

| | | | |
|---|---|---|---|
| FR | 3087869 A1 * | 5/2020 | ............ A61M 39/12 |
| JP | S53-60715 A | 5/1978 | |
| JP | S61-200984 U | 12/1986 | |
| JP | H01-230373 | 9/1989 | |
| JP | 6313059 | 11/1994 | |
| JP | H11-502597 | 3/1999 | |
| JP | 2005198858 | 7/2005 | |
| JP | 2007508103 | 4/2007 | |
| JP | 2010054052 | 3/2010 | |
| JP | 2010530943 | 9/2010 | |
| JP | 2011000132 | 1/2011 | |
| JP | 2014095461 | 5/2014 | |

OTHER PUBLICATIONS

Chinese Office Action for Chinese App. No. 201880089726.3, dated Sep. 23, 2021, 33 pages.
Extended European Search Report for European App. No. 18902243.7, dated Jul. 28, 2021.
Japanese Office Action for App. No. 2020-560861, dated Dec. 13, 2021, 14 pgs.
Chinese Office Action for App. No. 201880089726.3, dated May 5, 2022, 16 pages.
Japanese Office Action for App. No. 2020560861, dated Jul. 29, 2022, 9 pgs.

* cited by examiner

FLUID TRANSFER ASSEMBLY

FIELD OF THE DISCLOSURE

The present disclosure relates to fluid transfer fittings and assemblies, for example aseptic fluid transfer assemblies suitable for facilitating fluid flow from a source to a destination.

BACKGROUND

Biopharmaceutical and pharmaceutical drug developers and manufactures often develop and manufacture products in a fluid form. These products must be handled with care to maintain an aseptic environment and avoid contamination. Drugs developed and produced by biopharmaceutical and pharmaceutical companies are often produced through a multitude of steps that may require transfer of the fluids between one or more of the steps. In addition, samples are often drawn from each batch throughout the manufacturing process to keep a close watch on characteristics, including but not limited to, cell viability, density and characterization, fluid chemistry, pH, and sterility.

The manufacturing and testing processes required by biopharmaceutical and pharmaceutical companies create significant opportunities for fluid transfer. Each occurrence of fluid transfer that relies upon separate containers, conduits, or components to leave the source and arrive at the destination creates an opportunity for leaks or contamination.

The present disclosure describes improvements fluid transfer assemblies to maintain aseptic environments and avoid contamination during fluid transfer.

SUMMARY

One embodiment of the present disclosure includes a fluid transfer assembly that includes a fitting comprising a lumen having an opening, and at least one barb, the at least one barb extending circumferentially around the lumen proximate to the opening. The assembly also includes a flexible conduit, a deformable sleeve, and an elastomeric liner disposed between the sleeve and the conduit. The fitting extends at least partially into the conduit such that the conduit extends over the at least one barb. The elastomeric liner applies substantially 360 degree radial pressure to the conduit such that the conduit is sealingly compressed around the at least one barb of the fitting. The assembly is fluid tight up to a burst pressure of the conduit.

Another embodiment of present disclosure includes a collar for sealing a flexible conduit to a fluid transfer fitting that has at least one barb and a surface irregularity. The collar comprises a metallic sleeve configured to be permanently deformably crimped around a location of overlap between the flexible conduit and the fitting, and an elastomeric liner attached to an interior surface of the sleeve.

Another embodiment of the present disclosure includes a method of sealing a flexible conduit to a fluid transfer fitting. The method comprises inserting a portion of the fluid transfer fitting, including at least one barb, into an end of the flexible conduit. The method also includes positioning a collar around a location where the flexible conduit overlaps the fluid transfer fitting, the collar comprising a metallic sleeve, and an interior elastomeric liner. The method also includes crimping the collar around the flexible conduit and the fluid transfer fitting such that an inner surface of the flexible conduit conforms to any exterior surface irregularities of the fitting. Crimping the collar around the flexible conduit and fluid transfer fitting compresses the inner surface of the flexible conduit against the fitting to form a seal therewith.

These and other aspects of the present invention will become apparent to those skilled in the art after a reading of the following description of the preferred embodiments, when considered in conjunction with the drawings. It should be understood that both the foregoing general description and the following detailed description are explanatory only and are not restrictive of the invention as claimed.

DETAILED DESCRIPTION

Exemplary embodiments of this disclosure are described below and illustrated in the accompanying figures, in which like numerals refer to like parts throughout the several views. The embodiments described provide examples and should not be interpreted as limiting the scope of the invention. Other embodiments, and modifications and improvements of the described embodiments, will occur to those skilled in the art and all such other embodiments, modifications and improvements are within the scope of the present invention. Features from one embodiment or aspect may be combined with features from any other embodiment or aspect in any appropriate combination. For example, any individual or collective features of method aspects or embodiments may be applied to apparatus, product or component aspects or embodiments and vice versa.

Figure 1:
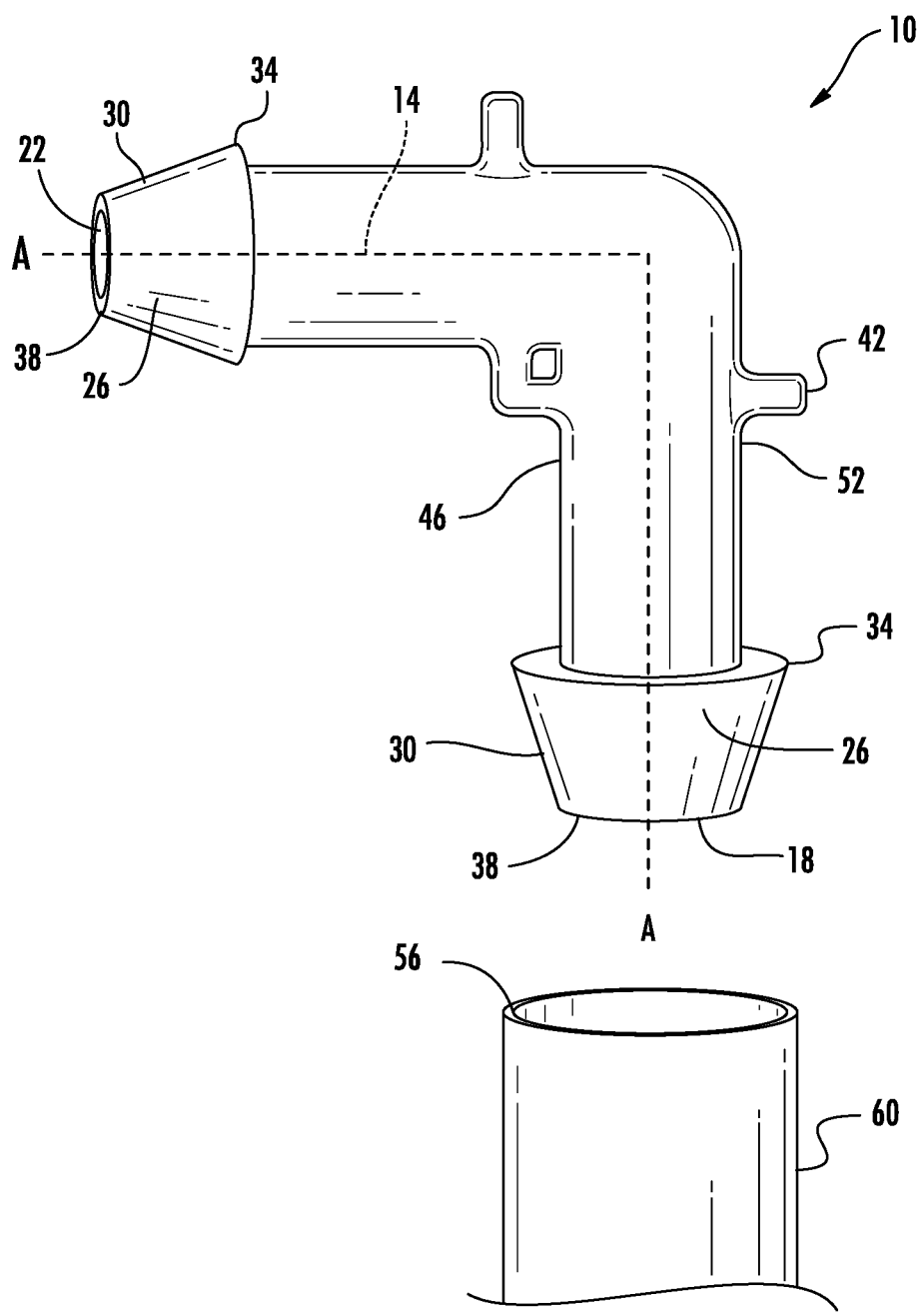
FIG. 1 shows a conventional fitting suitable for use with embodiments of the present disclosure.

FIG. 1 shows a fitting 10. The illustrated fitting 10 is an elbow fitting, but the present disclosure is not limited to use with elbow fittings, but may also apply to linear arrangements or fittings that split or combine a flow of fluid therethrough. A lumen 14 may extend from a first opening 18 to a second opening 22 of the fitting 10. In the illustrated example, a barb 26 is provided proximate to each of the openings 18, 22. In other embodiments, a barb 26 is used adjacent to only one end of the lumen 14. In some embodiments, more than one barb 26 may be formed adjacent to one or more of the openings 18, 22. The barb 26 may extend circumferentially around the lumen 14. The barb 26 may provide a tapered surface 30 from a maximum diameter portion 34 of the barb toward an insertion end 38. In the illustrated embodiment, the insertion end 38 corresponds with the first opening 18. The fitting 10 may optionally include a shoulder 42 to limit a magnitude of insertion of the insertion end 38 into a corresponding conduit. A shank 46, which may be substantially cylindrical, may be defined as the portion of the fitting 10 between the barb 26 and the shoulder 42.

The fitting 10 may be formed from molding, casting, additive manufacturing, or other known processes. The fitting may be made from thermoplastics such as polyolefins, polypropylene, polyethylene, polyoxymethylene (POM), polyvinylidenefluoride (PVDF), polytetrafluoroethylene (PTFE), polyamide, polysulfone, polyester, polycarbonate, and glass filled thermoplastics. The fitting may also be made from thermosets such as epoxies, pheonolics, silicone, copolymers of silicone and novolacs. Other suitable materials may include cyanate ester, polyurethanes, and urethane methacrylate. Yet other metallic materials may be used, for example stainless steel, aluminum, copper, and titanium.

Figure 6:
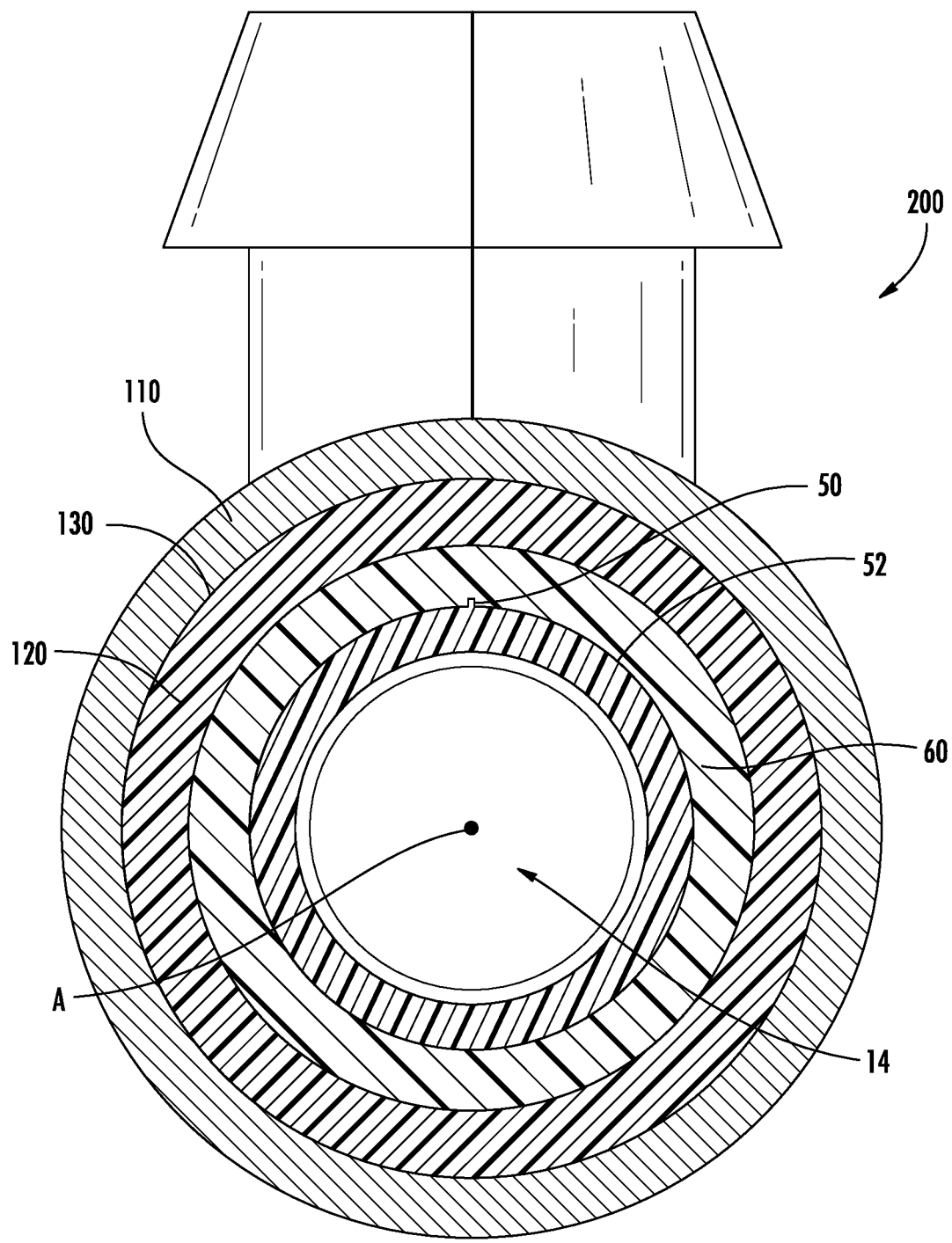
FIG. 6 shows a lateral cross section of the fluid transfer assembly of FIG. 5.

In some embodiments, the selected manufacturing process, the selected material, or some combination thereof, may lead to a surface irregularity 50 (see FIG. 6). For example, the surface irregularity 50 may constitute a raised seam along an exterior surface 52 of the fitting 10 that may extend along an axis A of the lumen 14. The surface irregularity 50 may be the result of the parting line between halves of a mold used to manufacture the fitting 10. The inventor has found that the surface irregularity 50 along the exterior surface 52 of the fitting 10 may increase the likelihood of a leak point between the fitting 10 and a corresponding conduit. Embodiments of the present disclosure seek to minimize the potential for leaks between a fitting 10 and a conduit.

The insertion end 38 of the fitting 10 is configured for insertion into a distal end 56 of a conduit 60 such that the conduit extends over the barb 26. The insertion end 38 of the fitting 10 may be inserted until the distal end 56 abuts the shoulder 42. The conduit 60 may preferably be a flexible conduit suitable for use in medical or pharmaceutical environments. The conduit 60 may be constructed of a thermoset or a thermoplastic polymer. If a thermoset is used, silicones, polyurethanes, fluoroelastomers or perfluoropolyethers are preferred construction materials for the conduits. If a thermoplastic is used, C-Flex® tubing, block copolymers of styrene-ethylene-butylene-styrene, PureWeld, PVC, polyolefins, or polyethylene are preferred construction materials. A conduit 60 constructed from ethylene-vinyl acetate (EVA) may be preferred due to the ability to weld together components made from EVA.

The conduit 60 may have an inner diameter selected for suitable use with the fitting 10 based upon the size of the lumen 14 and the wall thickness of the fitting. The conduit 60 may have an inner surface 62 (see FIGS. 4 and 5) and a wall thickness selected for its suitability to withstand internal fluid pressures depending upon the use of the conduit. The conduit 60 may be a single-walled conduit. Use of single-walled conduits may be preferred to minimize any interstitial space that could occur between the walls of multi-wall conduits, which could create opportunities for leaks or bacteria growth.

According to prior art embodiments, surface contact between the barb 26 and the conduit 60 sometimes provided sufficient retention of the conduit on the fitting 10. In other prior art embodiments, fasteners, such as cable ties or Oetiker clamps, were secured around the conduit 60 along the shank 46 of the fitting 10. The inventor has set out to provide an alternative embodiment for securing a conduit 60 to the barb 26 of a fitting 10. Preferably, the proposed embodiment creates a seal between the barb 26 and the conduit 60 to minimize fluid leaks therebetween.

Figure 2:
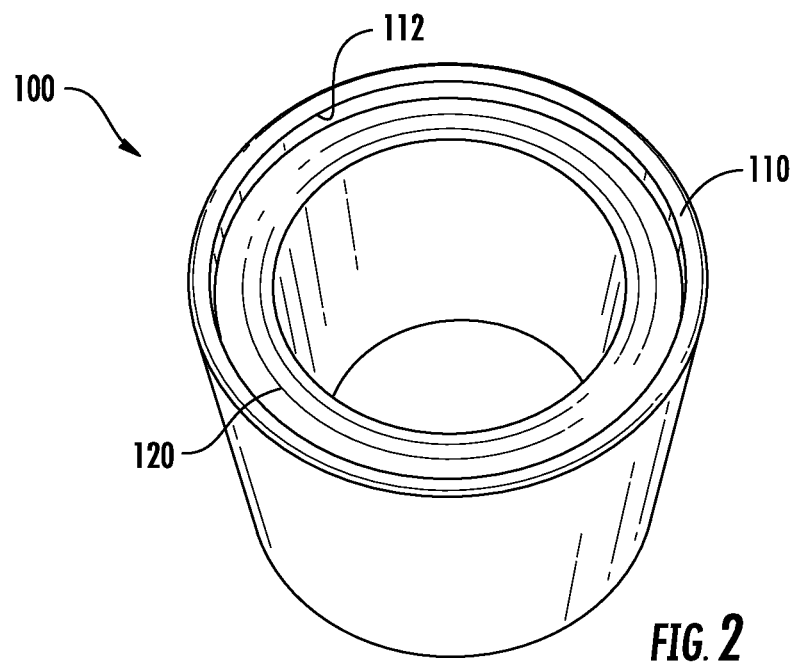
FIG. 2 shows a collar according to an embodiment of the present disclosure.
Figure 3:
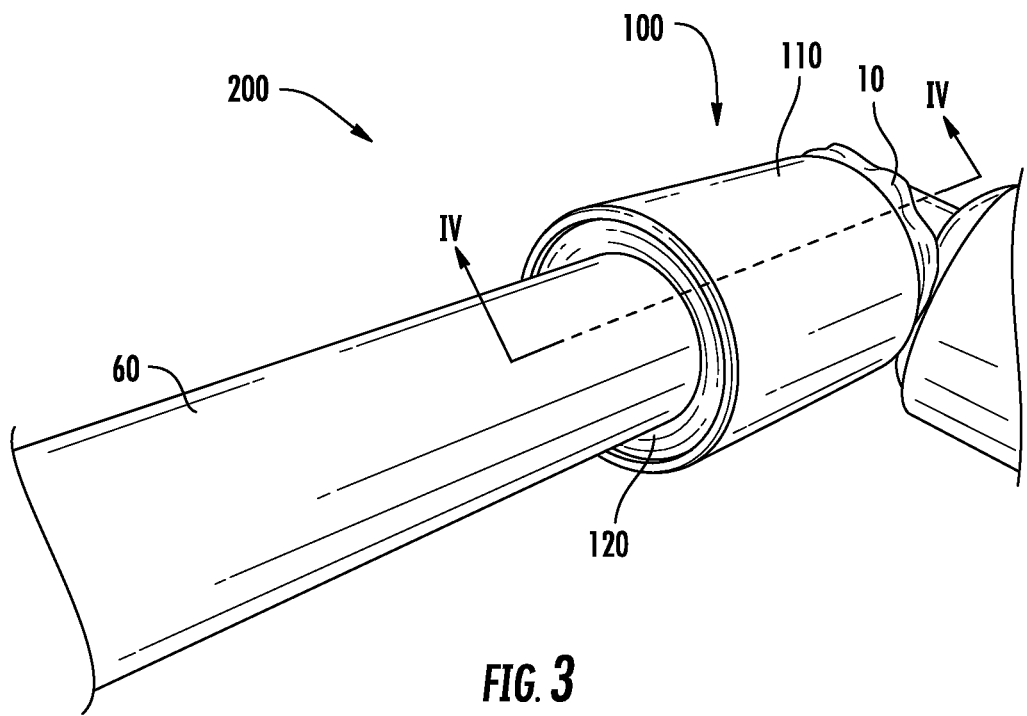
FIG. 3 shows a fluid transfer assembly according to an embodiment of the present disclosure.

FIG. 2 illustrates a collar 100 for sealing a conduit 60 (FIG. 1) to the barb 26 of the fitting 10. The collar 100 includes a metallic sleeve 110 and an elastomeric liner 120. The metallic sleeve 110 is preferably formed from steel or stainless steel with a wall thickness of about 0.010" to about 0.100". In one embodiment, the metallic sleeve was formed using 3161 stainless steel and a wall thickness of 0.049" and an outside diameter of 0.75". The metallic sleeve 110 provides a substantially rigid sleeve that may be permanently deformed using known crimping processes involving a hydraulic crimper. The metallic sleeve 110 is configured to surround the elastomeric liner 120. The elastomeric liner 120 may be attached to or separate from the metallic sleeve 110. In one embodiment, the elastomeric liner 120 is attached to an interior surface 112 of the metallic sleeve 110 with an adhesive layer 130 (FIG. 5).

The elastomeric liner 120 may be made from silicone (VMQ), or other materials such as phenyl silicone (PMVQ). Preferably, the elastomeric liner 120 maintains its elasticity at temperatures as low as –100° C. In one embodiment, the elastomeric liner 120 was formed from PMVQ using RTV MED-6010 from Nusil Technologies, Inc. in a layer with an uncompressed thickness of 0.062".

Figure 4:
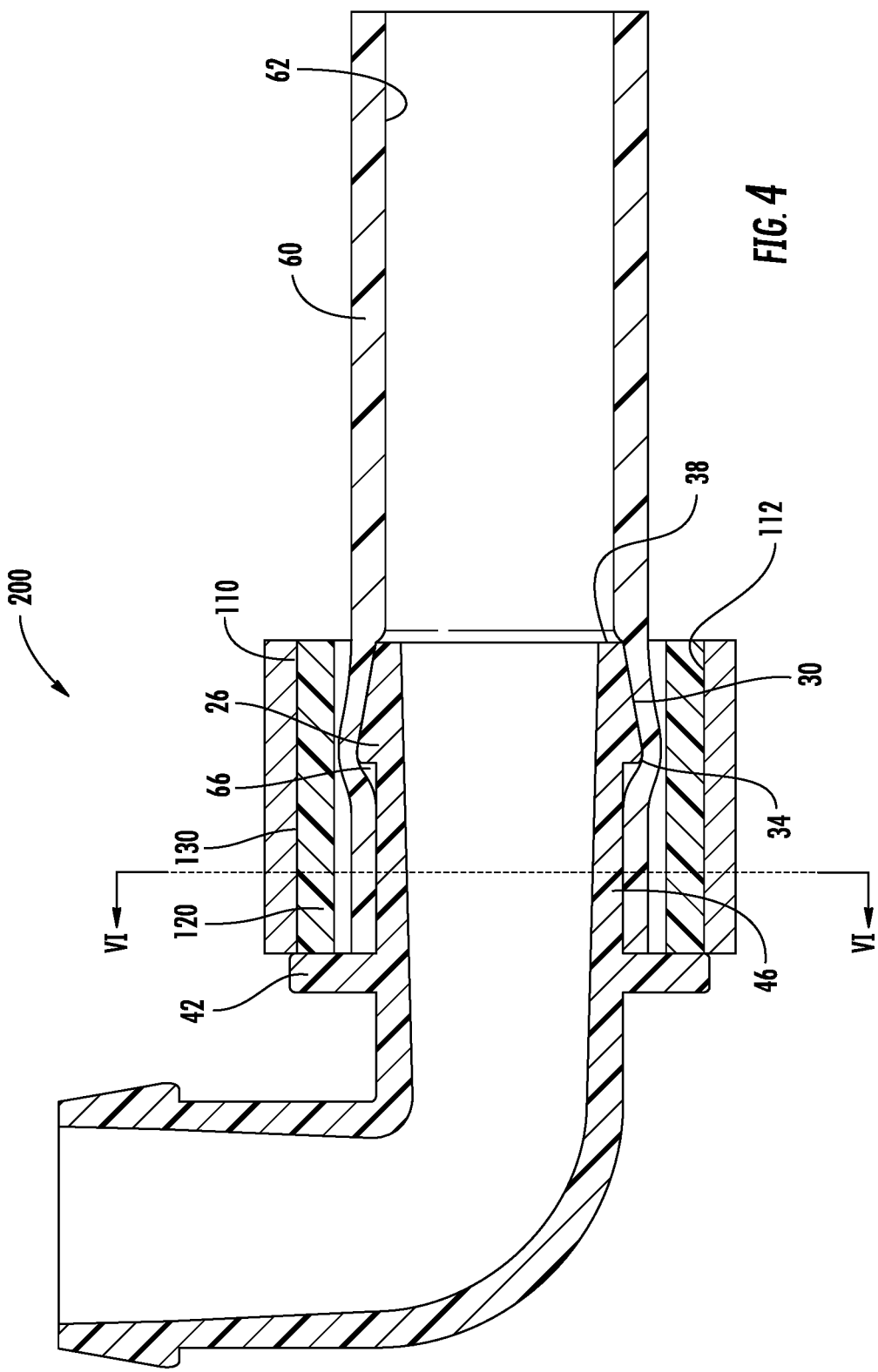
FIG. 4 shows a longitudinal cross section of the fluid transfer assembly of FIG. 3 before the collar is crimped.
Figure 5:
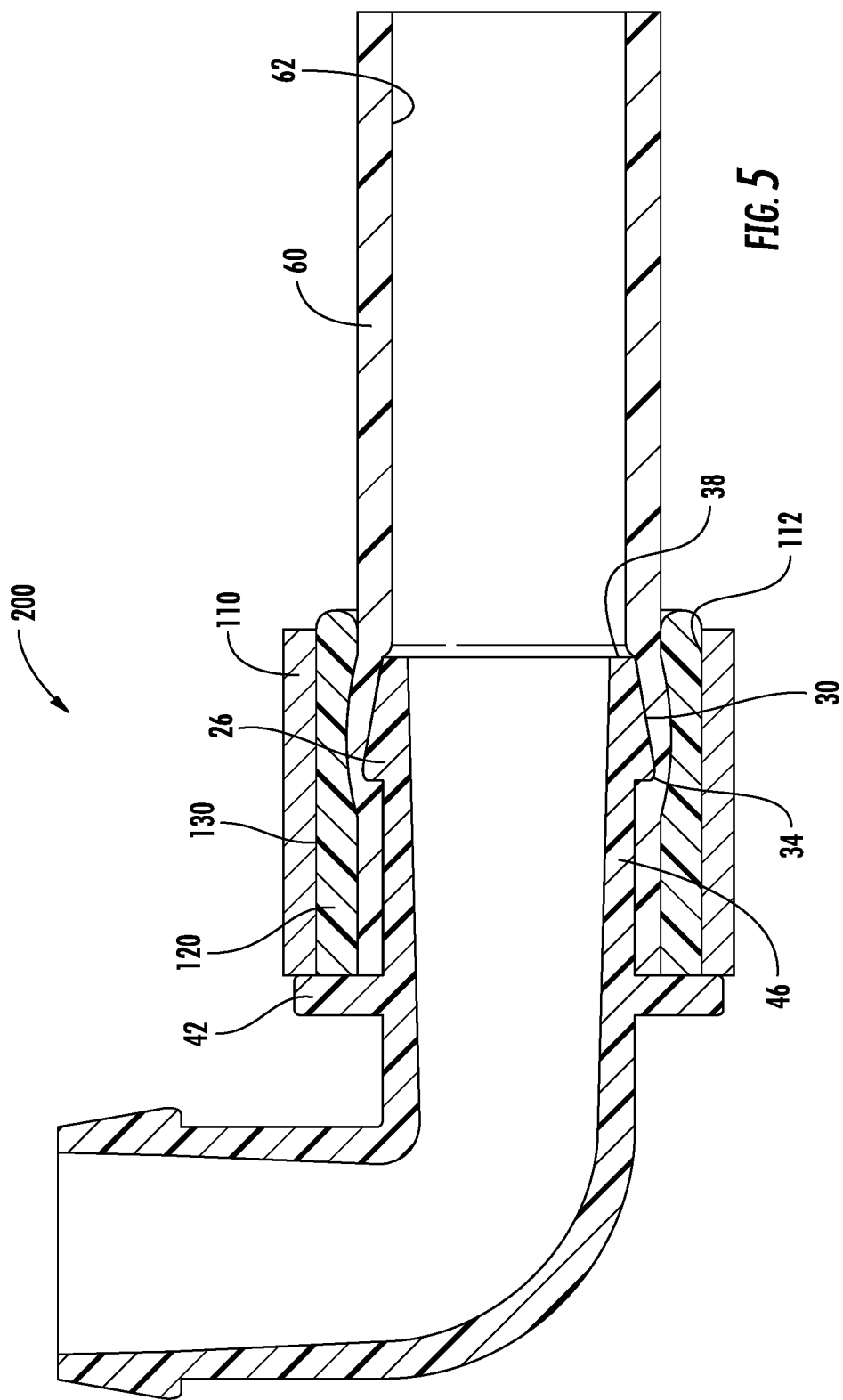
FIG. 5 shows a longitudinal cross section of the fluid transfer assembly of FIG. 3 after the collar is crimped.

The collar 100 is intended to be positioned around the conduit 60 and the fitting 10 as shown in FIGS. 3-6 to form a fluid transfer assembly 200. Once positioned at the desired location along the fitting 10, the collar 100, and particularly the metallic sleeve 110, can be substantially permanently deformed with a hydraulic crimper to reduce an inner diameter of the metallic sleeve 110 and apply a compression force on the elastomeric liner 120. FIG. 4 illustrates the placement of the collar before being crimped, and FIG. 5 illustrates the resulting cross-section after being crimped. In one embodiment, a Finn-power hydraulic crimper (model P32) was set to apply a force sufficient to reduce the outside diameter of the sleeve 110 to 0.700". One skilled in the art will appreciate that the hydraulic crimper would render the collar 100 as a single-use fastener that would not be readily reusable and releasable from around the fitting 10.

The collar 100 is intended to be positioned around the portion of the conduit 60 that overlaps with and surrounds the barb 26. Therefore, unlike traditional fasteners that are configured to encircle the shank 46 of the fitting 10, the collar 100 is configured to fasten and seal the conduit 60 to the barb 26 of the fitting 10. For example, the elastomeric liner 120 may be configured to maintain the conduit 60 compressed onto the tapered surface 30 of the barb 26 to form a seal between the barb and an inner surface 62 of the conduit 60. In addition, as shown in FIG. 4, an air gap 66 may be created between the conduit 60 and the exterior surface 52 adjacent to the maximum diameter portion 34 when the conduit 60 is first inserted over the barb 26. This air gap 66 may produce a leak point if the conduit is fastened with a conventional fastener. With the collar 100 of the present disclosure, however, once the metallic sleeve 110 is crimped (FIG. 5), the air gap may be eliminated. Also, once crimped, the elastomeric liner 120 applies substantially 360 degree radial pressure to the conduit 60 such that the conduit is sealingly compressed to the barb 26 of the fitting 10. The described arrangement renders the fluid transfer assembly 200 fluid tight up to a burst pressure of the conduit 60.

The elastomeric liner 120 is configured to provide a compliant material that is capable of taking up differences in the gap between the metallic sleeve 110 and the conduit 60. As a result, the elastomeric liner 120 improves the uniformity of the compression forces acting upon the conduit 60 and the barb 26. The use of the elastomeric liner 120 increases the ability of the collar 100 to secure the conduit 60 to the fitting 10 in a manner that compensates for any surface irregularities 50 (FIG. 6) on the fitting. In effect, the pressure applied by the elastomeric liner 120 conforms the conduit 60 around the exterior surface irregularity 50 of the fitting 10 to minimize leaks, including the potential to minimize or eliminate the presence of any air gaps 66 as discussed above.

The structure of the collar 100 and the fluid transfer assembly 200 may provide for novel uses or assembly processes. For example, use of the collar 100 as described above may provide for a method of sealing a conduit 60 to a fluid transfer fitting 10 comprising inserting a portion of the fluid transfer fitting, including at least one barb 26, into an end of the conduit. The method may further include positioning the collar 100 around a location where the conduit 60 overlaps the fluid transfer fitting 10. In one embodiment, the collar 100 may be positioned to surround the at least one barb 26 with at least a portion of an elastomeric liner 120 of the collar 100. In one embodiment, the collar 100 can surround substantially an entire length of overlap between the conduit 60 and the fitting 10. The method may also include crimping the collar 100 around the conduit 60 and the fluid transfer fitting 10 such that the inner surface 62 of the conduit conforms to any exterior surface irregularities 50 of the fitting. The step of crimping the collar 100 around the conduit 60 and fluid transfer fitting 10 may compress the inner surface 62 of the conduit 60 against the fitting 10 to form a seal therewith. In one example, the inner surface 62 of the conduit 60 is compressed against a tapered surface 30 of the barb 26 by the collar 100.

In one embodiment, the fluid transfer assemblies 200 may be assembled, and then the entire assemblies or components thereof may be sterilized or rendered substantially aseptic by, for example, gamma radiation. Alternatively, the entire fluid transfer assemblies or components thereof may be rendered substantially aseptic by exposure to steam above 121° C. for a period of time long enough to eliminate microorganisms. The entire assemblies or components thereof may also be rendered aseptic by chemical treatment, such as with ethylene oxide (ETO). Once rendered substantially aseptic, the fluid transfer assemblies may be appropriately packaged and stored to maintain the substantially aseptic state until ready for use.

Although the above disclosure has been presented in the context of exemplary embodiments, it is to be understood that modifications and variations may be utilized without departing from the spirit and scope of the invention, as those skilled in the art will readily understand. Such modifications and variations are considered to be within the purview and scope of the appended claims and their equivalents.

The invention claimed is:

1. A fluid transfer assembly, comprising:
a fitting comprising a lumen having an opening, and at least one barb, the at least one barb extending circumferentially around the lumen proximate to the opening;
a flexible conduit; and
a collar comprising:
a deformable sleeve having an interior surface; and
an elastomeric liner adhered to the interior surface of the sleeve, the elastomeric liner disposed between the sleeve and the conduit when the collar is disposed over the conduit,
wherein the fitting extends at least partially into the conduit such that the conduit extends over the at least one barb,
wherein the elastomeric liner applies substantially 360 degree radial pressure to the conduit such that the conduit is sealingly compressed around the at least one barb of the fitting, and
wherein the assembly is fluid tight up to a burst pressure of the conduit.

2. The fluid transfer assembly of claim 1, wherein the at least one barb comprises a tapered surface from a maximum diameter portion toward an insertion end thereof, wherein the elastomeric liner is configured to maintain the conduit compressed onto the tapered surface to form a seal between the at least one barb and an inner surface of the conduit.

3. The fluid transfer assembly of claim 2, wherein the fitting has a parting line along an axis of the fitting that creates an exterior surface irregularity on the fitting, wherein the pressure applied by the elastomeric liner conforms the conduit around the exterior surface irregularity of the fitting to minimize leaks.

4. The fluid transfer assembly of claim 1, further comprising an adhesive layer disposed between the elastomeric liner and the sleeve.

5. The fluid transfer assembly of claim 1, wherein the elastomeric liner comprises silicone configured to maintain elasticity at −100° C.

6. The fluid transfer assembly of claim 5, wherein the elastomeric liner comprises PMVQ silicone.

7. The fluid transfer assembly of claim 1, wherein the conduit comprises a single wall comprising ethyl vinyl acetate.

8. The fluid transfer assembly of claim 1, wherein the sleeve comprises rigid stainless steel that is deformable with a hydraulic crimper to be permanently positioned around the conduit as a single-use component.

9. A method of sealing a flexible conduit to a fluid transfer fitting, comprising:
inserting a portion of the fluid transfer fitting, including at least one barb, into an end of the flexible conduit;
positioning a collar around a location where the flexible conduit overlaps the fluid transfer fitting, the collar comprising a metallic sleeve surrounding and adhered to an interior elastomeric liner; and
crimping the collar around the flexible conduit and the fluid transfer fitting such that an inner surface of the flexible conduit conforms to any exterior surface irregularities of the fitting,
wherein crimping the collar around the flexible conduit and fluid transfer fitting compresses the inner surface of the flexible conduit against the fitting to form a seal therewith.

10. The method of claim 9, further comprising sterilizing the collar, flexible conduit, and fluid transfer fitting.

11. The method of claim 9, further comprising adhering the interior elastomeric liner to an interior surface of the metallic sleeve before positioning the collar.

12. The method of claim 9, wherein positioning the collar further comprises surrounding the at least one barb with at least a portion of the interior elastomeric liner.

13. The method of claim 9, wherein positioning the collar further comprises surrounding substantially an entire length of overlap between the flexible conduit and the fluid transfer fitting.

14. The method of claim 9, wherein,
the at least one barb comprises a tapered surface from a maximum diameter portion toward an insertion end thereof, and
crimping the collar around the flexible conduit and fluid transfer fitting compresses the inner surface of the flexible conduit against the tapered surface.

15. The method of claim 9, wherein crimping the collar permanently deforms the metallic sleeve such that the collar is a single-use component.

* * * * *